(12) United States Patent
Cannell et al.

(10) Patent No.: US 8,956,358 B2
(45) Date of Patent: Feb. 17, 2015

(54) DEVICES, SYSTEMS AND METHODS FOR CUTTING BONE

(75) Inventors: Matthew Cannell, Rugby (GB); Nicholas Turner, Devizes (GB)

(73) Assignee: Smith & Nephew, PLC., London (GB)

( * ) Notice: Subject to any disclaimer, the term of this patent is extended or adjusted under 35 U.S.C. 154(b) by 293 days.

(21) Appl. No.: 12/674,535

(22) PCT Filed: Aug. 22, 2008

(86) PCT No.: PCT/GB2008/002865
§ 371 (c)(1),
(2), (4) Date: Mar. 24, 2010

(87) PCT Pub. No.: WO2009/024798
PCT Pub. Date: Feb. 26, 2009

(65) Prior Publication Data
US 2011/0118743 A1 May 19, 2011

(30) Foreign Application Priority Data

Aug. 23, 2007 (GB) .................................. 0716464.3

(51) Int. Cl.
*A61B 17/00* (2006.01)
*A61B 17/16* (2006.01)
(52) U.S. Cl.
CPC ......... *A61B 17/1668* (2013.01); *A61B 17/1633* (2013.01); *A61B 17/1617* (2013.01); *A61B 17/162* (2013.01)
USPC .................................. 606/80; 606/79; 408/67
(58) Field of Classification Search
USPC .................... 606/79–82, 84; 408/67
See application file for complete search history.

(56) References Cited

U.S. PATENT DOCUMENTS

| 4,111,208 A | * | 9/1978 | Leuenberger | 606/80 |
|---|---|---|---|---|
| 4,116,200 A | * | 9/1978 | Braun et al. | 606/81 |
| 5,292,210 A | * | 3/1994 | Nowick | 408/67 |
| 5,489,310 A | | 2/1996 | Mikhail | |
| 5,501,686 A | * | 3/1996 | Salyer | 606/79 |
| 5,885,298 A | | 3/1999 | Herrington et al. | |
| 5,913,859 A | * | 6/1999 | Shapira | 606/80 |
| 6,071,284 A | * | 6/2000 | Fox | 606/80 |
| 6,162,227 A | | 12/2000 | Eckhardt et al. | |

(Continued)

FOREIGN PATENT DOCUMENTS

| EP | 1764046 | 3/2007 |
|---|---|---|
| EP | 2197365 | 6/2010 |

(Continued)

OTHER PUBLICATIONS

Communication dated Sep. 23, 2010 issued by the European Patent Office in Patent Application No. 08788425.0.

*Primary Examiner* — Matthew Lawson
*Assistant Examiner* — Si Ming Le
(74) *Attorney, Agent, or Firm* — Ropes & Gray LLP

(57) ABSTRACT

Devices, systems, and methods are provided for cutting bone and collecting bone debris. A disclosed device includes a receptacle having a proximal opening, a cutting tool having a connector on a proximal end, and a space between the cutting tool and receptacle. In use, bone debris produced by the cutting tool is received by the receptacle into the space. A distal opening of the receptacle may have dimensions corresponding to those of the cutting tool. The receptacle may be shaped so that it does not extend beyond the outer periphery of the cutting tool.

25 Claims, 5 Drawing Sheets

(56) References Cited

U.S. PATENT DOCUMENTS

| | | |
|---|---|---|
| 6,283,971 B1 | 9/2001 | Temeles |
| 6,325,806 B1 | 12/2001 | Fox |
| 6,730,094 B2 * | 5/2004 | Salyer et al. .................... 606/80 |
| 6,890,336 B2 * | 5/2005 | Nordman ........................ 606/80 |
| 7,033,359 B2 * | 4/2006 | Meller ............................ 606/80 |
| 7,850,691 B2 * | 12/2010 | Lechot ............................ 606/81 |
| 2003/0078586 A1 * | 4/2003 | Shapira .......................... 606/80 |
| 2003/0130741 A1 * | 7/2003 | McMinn .................... 623/23.14 |
| 2003/0135217 A1 | 7/2003 | Buttermann et al. |
| 2004/0210229 A1 | 10/2004 | Meller |
| 2005/0251145 A1 * | 11/2005 | Desarzens et al. ............. 606/80 |

FOREIGN PATENT DOCUMENTS

| | | |
|---|---|---|
| WO | WO9947051 | 9/1999 |
| WO | WO2009/024798 | 2/2009 |

* cited by examiner

DEVICES, SYSTEMS AND METHODS FOR CUTTING BONE

CROSS REFERENCE TO RELATED APPLICATIONS

This application is the U.S. national phase of International Application No. PCT/GB2008/002865 filed on Aug. 22, 2008 and published in English on Feb. 26, 2009 as International Publication No. WO 2009/024798 A1, which application claims priority to Great Britain Application No. 0716464.3 filed on Aug. 23, 2007, the entire contents of both of which are incorporated herein by reference.

RELATED FIELDS

The present invention relates to medical devices, in particular devices for collecting bodily matter created during a surgical operation. Devices in accordance with the present invention may collect debris generated during cutting of a bone.

BACKGROUND

During orthopaedic surgery, debris from bone and cartilage is created by the instruments used to prepare the bone, for example cutting tools such as reamers. For example, during a hip resurfacing operation, bone debris is created from the instruments used to prepare the femoral head to the required dimensions. Hip resurfacing procedures involve reaming the femoral head and drilling a centralized stem hole. These procedures produce a significant amount of bone debris which is dispersed widely in the surrounding tissues. The greatest amount of debris is created when using a chamfer cutter.

Bone debris is problematic in a surgical site for a number of reasons. The debris can obstruct the surgeon's view of the surgical site, which may compromise the operation. The debris can also compromise the operation of surgical instruments, for example by getting caught in any moving parts. It is also essential during surgery to keep the wound clean. Bone debris may lead to heterotopic ossification. Moderate to severe heterotopic ossification can negate the benefits of replacement surgery and reducing bone debris has been shown to reduce the incidence of heterotopic ossification.

It is known to cover the surgical site with swabs in order to minimise the amount of bone debris entering the surgical site. For example, during hip resurfacing the area below the femoral neck is commonly covered using swabs in order to minimise the amount of bone debris entering the acetabulum. However, swabs can also obstruct the surgeon's view of the surgical site. Swabs can also compromise the operation of surgical instruments because the fibres of the swab can get caught in moving parts, for example a femoral reamer.

In addition to the use of swabs, the wound needs to be fully cleaned on completion of the operation in order to remove any bone debris or swab fibres.

SUMMARY

It is an aim of the present invention to provide a device for collecting bodily matter such as bone debris from a surgical site that overcomes one or more of the problems associated with known surgical techniques.

In some embodiments, there is provided a device for collecting bone debris, comprising: a receptacle having an opening, the receptacle opening being disposed with respect to a cutting tool such that, in use, bone debris produced by the cutting tool is received by the receptacle.

In some embodiments, there is provided a device for collecting bone debris, comprising: a receptacle having an opening, the receptacle opening being disposed with respect to the cutting tool such that, in use, bone debris produced by the cutting tool is received by the receptacle, wherein the opening of the receptacle has dimensions corresponding to those of the cutting tool.

According to some embodiments, the receptacle may have an outer periphery that matches the outer periphery of the cutting tool.

According to some embodiments, the cutting tool has a substantially circular outer periphery and the receptacle has a substantially circular outer periphery, wherein the diameter of the outer periphery of the cutting tool is substantially the same as the diameter of the outer periphery of the receptacle.

In some embodiments, there is provided a device for collecting bone debris, comprising: a receptacle having an opening, the receptacle opening being disposed with respect to the cutting tool such that, in use, bone debris produced by the cutting tool is received by the receptacle, wherein the cutting tool has an outer periphery and the receptacle is shaped so that it does not extend beyond the outer periphery of the cutting tool.

According to some embodiments, the diameter of the receptacle does not extend beyond the diameter of the cutting tool.

According to some embodiments, the diameter of the receptacle is substantially the same or less than the diameter of the cutting tool.

In some embodiments, there is provided a kit of parts, comprising: a receptacle as summarized above; and a plurality of cutting tools as summarized above, the cutting tools differing in size.

The kit of parts may provide a modular system in which a particular receptacle fits (is compatible with) multiple cutting tools of different sizes. Modular systems may also be provided comprising a plurality of receptacle sizes, each receptacle being compatible with a plurality of cutting tools. For example, the or each receptacle may be compatible with three different size cutting tools.

In some embodiments, there is provided a device for cutting bone, comprising:
   a cutting portion having a distal surface and a proximal surface, wherein the distal surface has at least one cutting means; and
   a receptacle disposed with respect to the proximal surface of the cutting portion such that, in use, bone debris produced by the cutting portion is received by the receptacle.

According to some embodiments, the cutting portion comprises at least one conduit disposed such that bone can move through the cutting portion from the distal surface to the receptacle via the or each conduit.

According to some embodiments, at least one conduit forms a cutting means on the distal surface of the cutting portion.

Devices according to some of the above embodiments have a number of advantages. They collect bone debris as it is produced by the cutting tool. Accordingly, bone debris is not dispersed into the surgical site and surrounding tissues. The surgeon therefore does not have to rely on swabs and thorough cleaning. The surgeon can also perform the operation without obstruction of his view of the surgical site. The risk of bone debris becoming caught in moving parts is also minimised, if not eliminated. Furthermore, the risk of heterotopic ossification is also minimised, if not eliminated.

Devices according to some of the above embodiments may also have the advantage that the receptacle is securely connected to the cutting tool during operation of the instrumentation. There is therefore no risk of the receptacle becoming detached accidentally and discarding the bone debris into the surgical site. The rigid and secure connections provided by devices according to the present invention optimise repeated operation of the cutting devices.

Embodiments of the present invention wherein the opening of the receptacle has dimensions corresponding to those of the cutting tool and/or wherein the receptacle is shaped so that it does not extend beyond the outer periphery of the cutting tool (FIG. 5), may have an advantage in that they may be optimal for a less invasive surgical approach. Such embodiments may add minimum amount of bulk to the cutting tool, thereby optimising them for minimally invasive surgery.

Furthermore, according to some embodiments, the devices are reusable after appropriate sterilisation.

The following features and embodiments may apply to one or more of the above embodiments, as appropriate.

According to some embodiments, the device is a receptacle that is releasably attachable to a cutting tool.

According to some embodiments, the device comprises a receptacle fixedly attached to a cutting tool.

The cutting tool may comprise one or more cutting surfaces and a drive shaft. The device may be disposed between the cutting surface(s) and the drive shaft.

The receptacle and the cutting tool may be formed as a single piece. That is, the receptacle, cutting surface and drive shaft may be formed as a single piece.

The receptacle and the cutting surface may be formed as a single piece. The drive shaft may be attachable to the receptacle and cutting surface.

The cutting tool may be a reamer. The reamer may be a chamfer cutter. The reamer may be a profile cutter.

The receptacle opening may be shaped so as to mate with the peripheral edge of the proximal surface of a reamer.

The cutting tool may be a sleeve cutter.

The receptacle opening may be shaped so as to mate with the peripheral edge of the proximal end of the sleeve cutter.

The receptacle may be fixedly attached to the cutting surface.

The receptacle may be fixedly attached to the cutting surface and the drive shaft.

The receptacle may be releasably attached to at least one of the cutting surface and the drive shaft.

The receptacle may comprise a second opening, or further openings, such as opening 22 in FIG. 5 for removal of bone debris from the receptacle.

The receptacle may comprise a cylinder. The cylinder may be an open cylinder. The cylinder may be partially closed at one or both ends. The cylinder may be closed at a first end and open at a second end.

The cylinder may have an outside diameter in the range 45 to 75 mm. The cylinder may have an outside diameter in the range 50 to 70 mm. The cylinder may have an outside diameter in the range 55 to 65 mm. The cylinder may have an outside diameter of around 60 mm.

The cylinder may have a length (height) in the range 15 to 50 mm. The cylinder may have a length in the range 15 to 45 mm. The cylinder may have a length in the range 20 to 45 mm. The cylinder may have a length in the range 20 to 40 mm. The cylinder may have a length in the range 20 to 35 mm. The cylinder may have a length in the range 20 to 30 mm. The cylinder may have a length of around 25 mm.

The device may be made of metal. The device may be made of metal alloy. The device may be made of titanium. The device may be made of a titanium alloy. The device may be made of stainless steel. The device may be made of cobalt chrome alloy.

The device may be made of plastic. The device may be made of polyethylene. The device may be made of polypropylene. The device may be made of polyacetal. The device may be made of polyphenylsulfone.

In some embodiments, there is provided a method of cutting a bone, comprising the steps of:
 providing a cutting tool;
 providing a receptacle, the receptacle having an opening;
 disposing the receptacle with respect to the cutting tool such that, in use, bone debris produced by the cutting tool is received by the receptacle via the opening; and
 cutting the bone with the cutting tool and thereby collecting bone debris in the receptacle.

In some embodiments, there is provided a method of cutting a bone, comprising the steps of:
 providing a receptacle and cutting tool according to one of the above-described embodiments;
 engaging the cutting tool with a bone; and
 cutting the bone and thereby collecting bone debris in the receptacle.

In some embodiments, there is provided a method of cutting a bone, comprising the steps of:
 providing a device for cutting bone according to one of the above-described embodiments;
 engaging the cutting portion with a bone; and
 cutting the bone and thereby collecting bone debris in the receptacle.

BRIEF DESCRIPTION OF THE DRAWINGS

Reference will now be made, by way of example, to the accompanying drawings, in which.

DETAILED DESCRIPTION OF THE DRAWINGS

Figure 1:
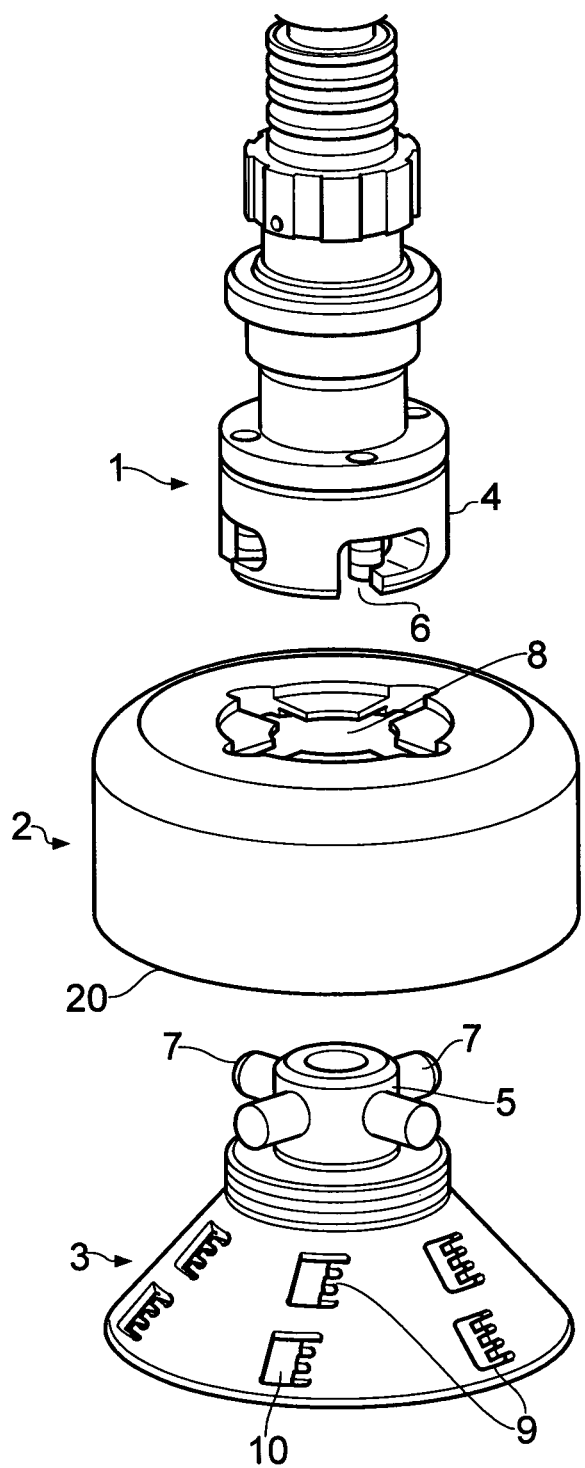
FIG. 1 shows a disassembled device according to an embodiment of the present invention.
Figure 2:
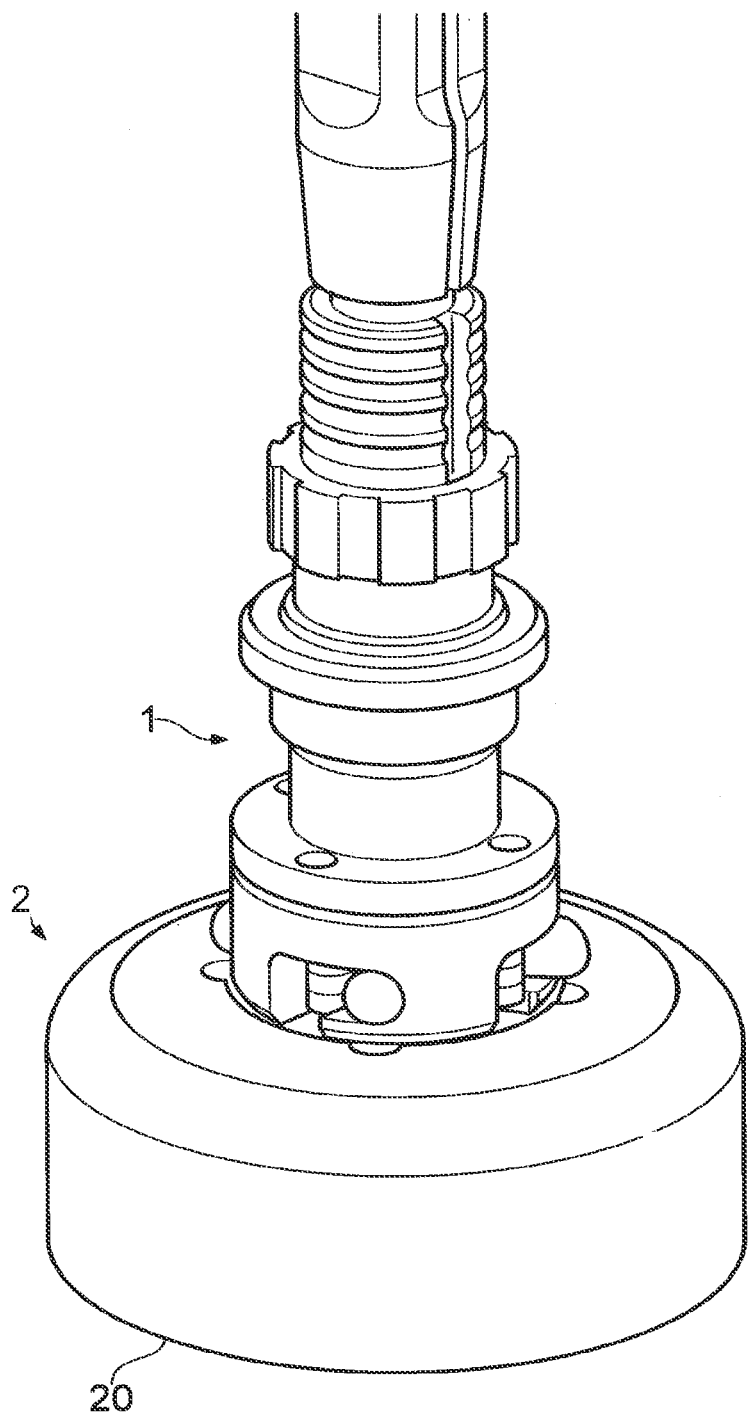
FIG. 2 shows the device of FIG. 1 when assembled.
Figure 3:
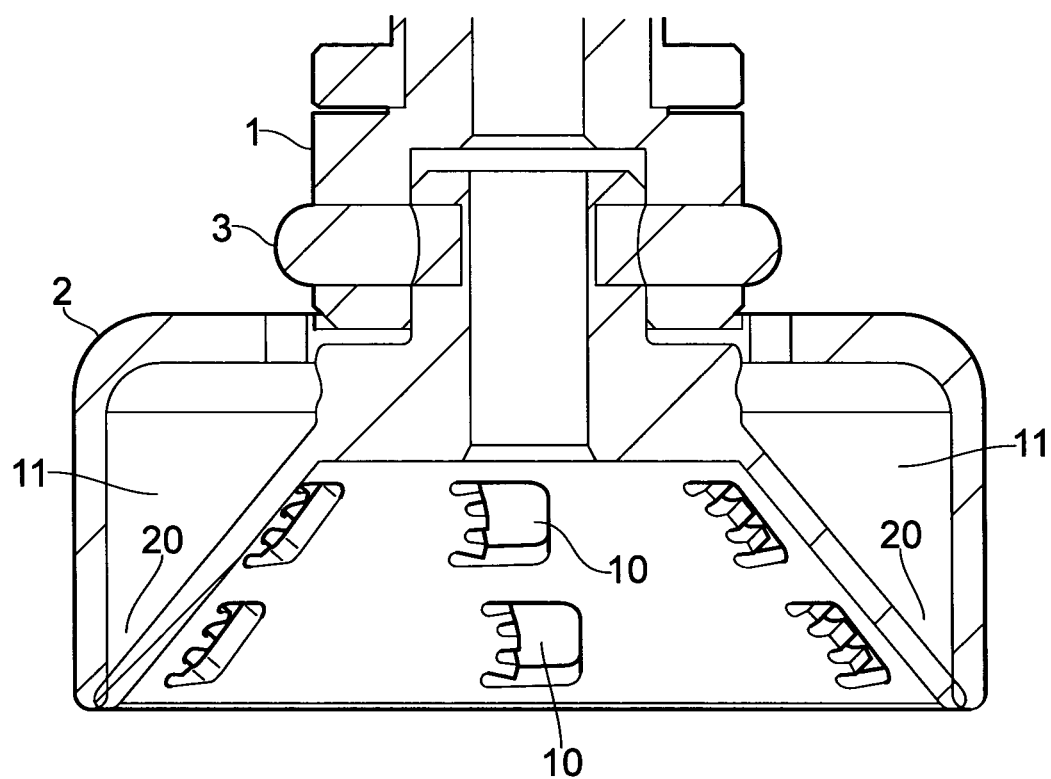
FIG. 3 shows a cross-sectional view of the device shown in FIG. 2.

As shown in FIGS. 1 to 3, the device comprises a modular drive shaft (1), a receptacle (2), and a cutting tool (3), which is a chamfer cutter in this particular embodiment. Other types of reamers or cutting instruments are in accordance with the present invention. For example, the cutting tool may be a reamer, such as an acetabular reamer. The cutting tool may be a sleeve cutter. The cutting tool may be a profile cutter.

In the embodiment shown in FIGS. 1 to 3, the components (1-3) are separable. The modular drive shaft (1) has a connector (4) at its distal end that engages with a connector (5) on the proximal end of the cutting tool (3). The connectors (4,5) may be in the form of a bayonet type connection, as shown in FIGS. 1 to 3. Connector (4) comprises one or more slots (6) or the like, and connector (5) comprises one or more pegs (7) or the like. When assembled, the one or more slots (6) receive the one or more pegs (7), thus forming the bayonet connection. In the embodiment shown in FIGS. 1 to 3, connector (4) comprises four slots (6) and connector (5) comprises four pegs (7). Other types of connection, such as a screw fit or friction fit, are also in accordance with the present invention.

The receptacle (2) has an opening (20) on its distal end that is shaped such that it fits over and accommodates the reverse face (proximal side) of the cutting tool (3), as shown in FIG. 3. The receptacle (2) has an opening (8) on its proximal end that is shaped such that the connector (5) of the cutting tool (3) passes through the opening (8) and engages with connector (4) such that the receptacle (2) is locked in place between the drive shaft (1) and the cutting tool (3), as shown in FIGS. 2 and 3. Drive shaft (1) imparts a torque to receptacle (2) and cutting tool (3) such that the cutting tool (3) rotates, causing the cutting means (serrated edge) (9) to cut bone when engaged with the bone. As shown in FIG. 3, bone debris will pass through the holes (10) and be collected in the space (11) formed between the cutting tool (3) and the receptacle (2).

Figure 4:
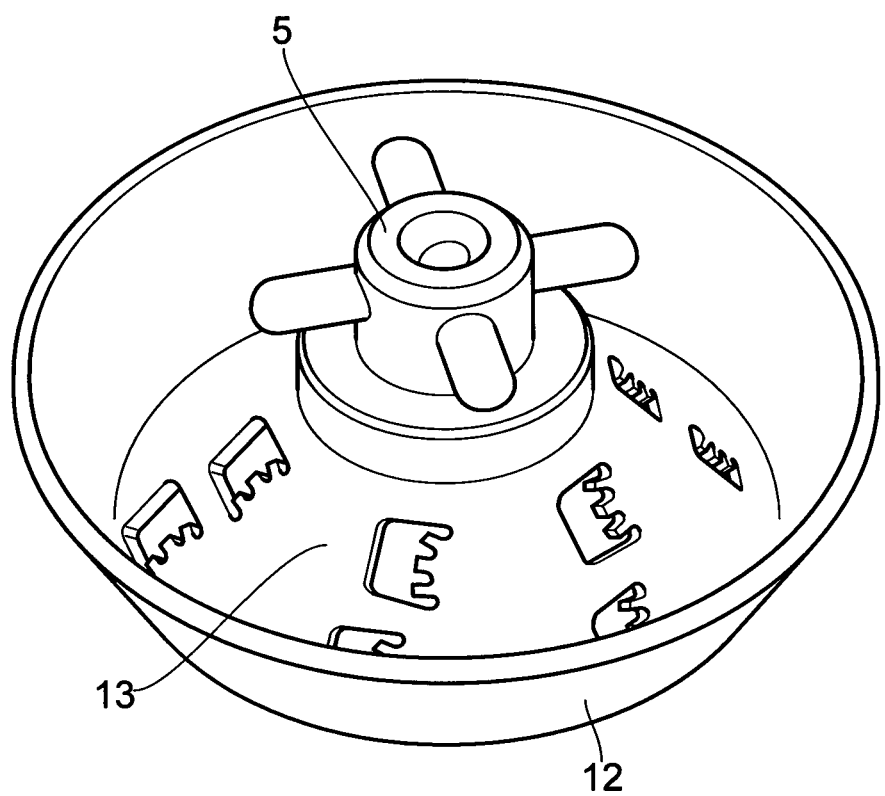
FIG. 4 shows a device according to another embodiment of the present invention.
Figure 5:
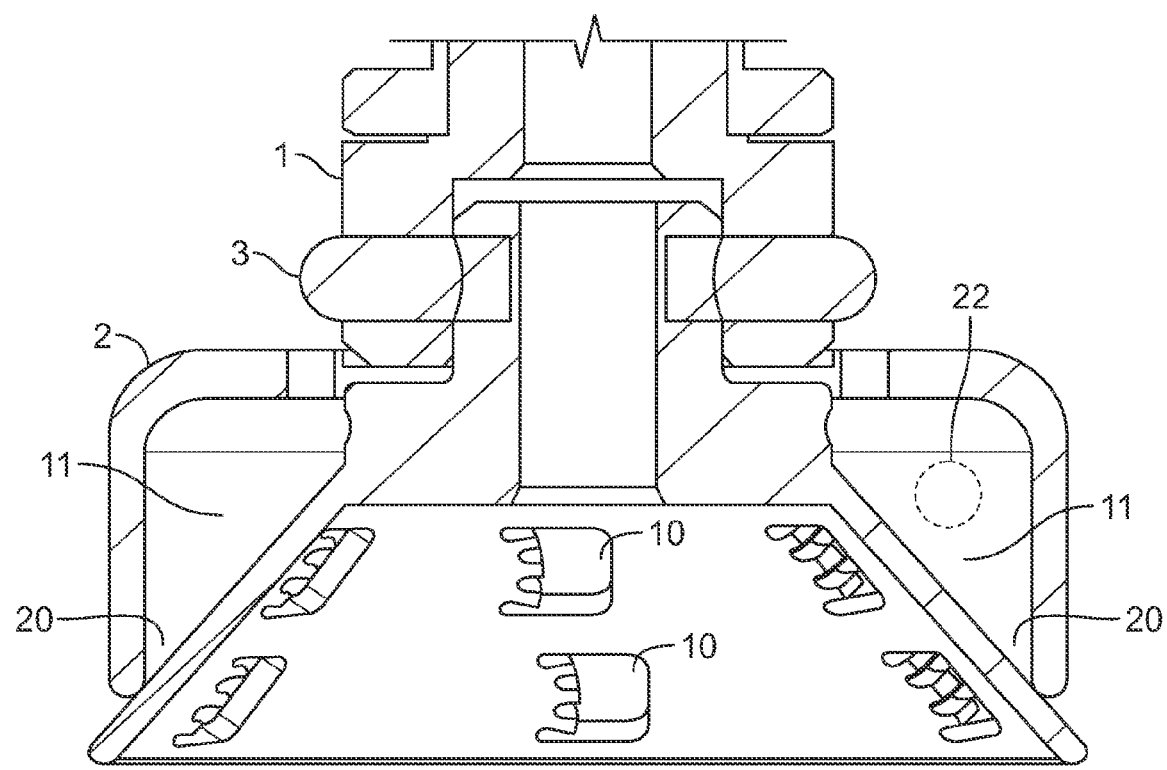
FIG. 5 shows a device according to another embodiment of the present invention.

FIG. 4 shows an alternative embodiment of the invention in which a receptacle (12) is fixedly attached to a cutting tool (13), which is a chamfer cutter in this particular embodiment. The receptacle (12) is attached to the peripheral edge of the proximal surface of the cutting tool (13). The cutting tool (13) has a connector (5) as in the embodiment shown in FIGS. 1 to 3 for connecting the cutting tool/receptacle (12,13) to a drive shaft (not shown).

Devices according to these embodiments may minimise, if not eliminate, the amount of bone debris entering the surgical site, by capturing the debris directly as it is produced from the cutting tool. The device is attached between the modular connection of the cutting tool and the drive shaft in order to ensure it is securely connected during the procedure. On completion of the cutting process the device can be removed and the debris discarded. This enables easy cleaning of the device and the cutting tool.

The procedure for using the device shown in FIGS. 1 to 3 comprises the following steps:
1. Position the receptacle (2) over the drive connector (5) on the reverse face (proximal side) of the cutting tool (3).
2. Connect the modular drive shaft (1) connector (4) to the cutting tool (3) connector (5), thereby securing the receptacle (2) in place.
3. Connect drive shaft (1) to a power tool and use the cutting tool (3) to prepare the bone, for example a femoral head. During this process the receptacle (2) will collect the bone debris created.
4. Remove the drive shaft (1), cutting tool (3) and receptacle (2) from the surgical site.
5. Remove the receptacle (2) and discard the bone debris.

The same principle of collecting bone debris could be easily adapted to use in other types of reamers or cutting instruments, including acetabular reamers, sleeve cutters and profile cutters.

The invention claimed is:

1. A device for collecting bone debris, comprising:
a cutting tool having a connector on a proximal end, a distal cutting surface, and a proximal surface positioned proximal to the distal cutting surface, wherein a through-hole extends from the distal cutting surface to the proximal surface;
a receptacle having a proximal opening sized and shaped for the connector of the cutting tool to releasably extend through the proximal opening of the receptacle and fit in rotational engagement with a drive shaft mount in a position that is surrounded at least in part by the proximal opening of the receptacle; and
a space disposed between the cutting tool and receptacle, such that, in use, bone debris produced by the cutting tool is received into the space via the through-hole, wherein the cutting tool has an outer periphery and the receptacle is shaped so that it does not extend beyond the outer periphery of the cutting tool.

2. The device of claim 1, wherein an outer periphery of the cutting tool is circular, and an outer periphery of the receptacle is circular.

3. The device of claim 1, wherein the receptacle has an outer periphery with a first diameter, and the outer periphery of the cutting tool has a second diameter, wherein the first diameter is less than the second diameter.

4. The device claim 1, wherein the receptacle is fixedly attached to the cutting tool.

5. The device of claim 1, wherein the receptacle is reversibly attached to the cutting tool.

6. The device of claim 1, wherein the receptacle is a cylinder with the proximal opening at a first end.

7. The device of claim 1, wherein the receptacle is disposed between the distal cutting surface and the drive shaft when the connector is in rotational engagement with the drive shaft.

8. The device of claim 7, wherein the receptacle is disposed between the proximal surface and the drive shaft when the connector is in rotational engagement with the drive shaft.

9. The device of claim 1, wherein the through-hole forms a cutting edge on the distal cutting surface of the cutting tool.

10. The device of claim 9, wherein the receptacle is fixedly attached to the distal cutting surface.

11. The device of claim 9, wherein the receptacle is fixedly attached to the distal cutting surface and the drive shaft.

12. The device of claim 9, wherein the receptacle is releasably attached to at least one of the distal cutting surface and the drive shaft.

13. The device of claim 1, wherein the cutting tool is a reamer.

14. The device of claim 13, wherein the reamer has a peripheral edge on the proximal surface, and the receptacle has a distal opening, wherein the distal opening of the receptacle is shaped so as to mate with the peripheral edge of the proximal surface of the reamer.

15. The device of claim 13, wherein the reamer is a chamfer cutter.

16. The device of claim 13, wherein the reamer is a profile cutter.

17. The device of claim 1, wherein the cutting tool is a sleeve cutter.

18. The device of claim 17, wherein the sleeve cutter has a peripheral edge on the proximal surface, and the receptacle has a distal opening, wherein the distal opening of the receptacle is shaped so as to mate with the peripheral edge of the proximal surface of the sleeve cutter.

19. The device of claim 1, wherein the receptacle further comprises a second opening for removal of bone debris from the receptacle.

20. The device of claim 1, wherein the connector has at least one peg.

21. A kit of parts, comprising:
a receptacle having a proximal opening; and
a plurality of cutting tools, each cutting tool having a distal cutting surface, a proximal surface positioned proximal to the distal cutting surface, and a through-hole that extends from the distal cutting surface to the proximal surface, wherein bone debris produced by each of the cutting tools is received into a space of the respective cutting tool via the respective through-hole, wherein each of the cutting tools has a proximal end with a connector, and wherein the proximal opening is sized and shaped for each connector of each cutting tool to releasably extend through the proximal opening of the receptacle and fit in rotational engagement with a drive shaft mount in a position that is surrounded at least in part by the proximal opening of the receptacle, and wherein each of the cutting tools differs in size, wherein each respective cutting tool has a respective outer periphery and the receptacle is shaped so that it does not extend beyond the respective outer periphery of the respective cutting tool.

22. A device for cutting bone, comprising:
a cutting portion comprising:
- a distal surface having a bone cutter;
- a proximal surface having a connector, wherein the connector extends from the proximal surface and is configured to engage a drive shaft mount; and
- a through-hole disposed through the distal surface and the proximal surface; and a receptacle disposed in a position that is proximal to the proximal surface of the cutting portion thereby forming a space disposed between the proximal surface and receptacle such that, in use, bone debris produced by the cutting portion is received into the space via the through-hole, wherein the receptacle comprises a proximal opening sized and shaped for the connector to extend through the proximal opening to engage the drive shaft mount in a position that is surrounded at least in part by the proximal opening of the receptacle, wherein the cutting portion has an outer periphery and the receptacle is shaped so that it does not extend beyond the outer periphery of the cutting portion.

23. The device of claim 22, wherein the through-hole forms the bone cutter on the distal surface of the cutting portion.

24. A method of cutting a bone, comprising the steps of:
providing a cutting tool having a through-hole extending from a distal surface to a proximal surface and a connector on a proximal end;

providing a receptacle having a proximal opening sized and shaped for the connector of the cutting tool to releasably extend through the proximal opening of the receptacle, wherein the cutting tool has an outer periphery and the receptacle is shaped so that it does not extend beyond the outer periphery of the cutting tool; and releasably fitting the connector with a mount on a drive shaft in a position that is surrounded at least in part by the proximal opening of the receptacle, thereby rotationally engaging the cutting tool with the drive shaft and forming a space disposed between the cutting tool and receptacle.

25. The method of claim 24, further comprising:
rotating the cutting tool;

engaging the cutting tool with a bone while rotating the cutting tool, thereby cutting the bone and forming bone debris;

passing the bone debris through the through-hole; and
collecting the bone debris in the space.

* * * * *